(12) United States Patent
Wurzbach

(10) Patent No.: US 11,846,625 B1
(45) Date of Patent: Dec. 19, 2023

(54) GREASE MEASUREMENT DEVICE AND METHOD

(71) Applicant: York Laboratories, LLC, York, PA (US)

(72) Inventor: Richard Wurzbach, Brogue, PA (US)

(73) Assignee: York Laboratories, LLC, York, PA (US)

( * ) Notice: Subject to any disclaimer, the term of this patent is extended or adjusted under 35 U.S.C. 154(b) by 197 days.

(21) Appl. No.: 17/586,752

(22) Filed: Jan. 27, 2022

Related U.S. Application Data

(60) Provisional application No. 63/142,096, filed on Jan. 27, 2021.

(51) Int. Cl.
    *G01N 33/28* (2006.01)
    *G01N 27/74* (2006.01)
    *G01N 1/14* (2006.01)

(52) U.S. Cl.
    CPC .......... *G01N 33/2888* (2013.01); *G01N 1/14* (2013.01); *G01N 27/74* (2013.01); *G01N 33/2894* (2013.01); *G01N 2001/1427* (2013.01)

(58) Field of Classification Search
CPC ........ G01N 33/26; G01N 33/28; G01N 33/30; G01N 33/2888; G01N 33/2894; G01N 2001/1427
See application file for complete search history.

(56) References Cited

U.S. PATENT DOCUMENTS

| | | | |
|---|---|---|---|
| 7,984,661 B2 | 7/2011 | Wurzbach | |
| 10,627,387 B1 | 4/2020 | Wurzbach et al. | |
| 2005/0181512 A1* | 8/2005 | Wollenberg | G01N 33/2888 436/60 |
| 2010/0109686 A1* | 5/2010 | Zhe | G01N 33/2888 324/698 |
| 2013/0333449 A1* | 12/2013 | Barraclough | G01N 33/2888 73/61.71 |
| 2017/0102308 A1 | 4/2017 | Gillette, II et al. | |
| 2020/0009549 A1* | 1/2020 | Hammes | B01F 33/406 |

* cited by examiner

*Primary Examiner* — Nathaniel J Kolb
(74) *Attorney, Agent, or Firm* — Hooker & Habib, P.C.

(57) ABSTRACT

A method and a device for obtaining and measuring at least one physical property of a sample of grease obtained from a reservoir of grease includes attaching the barrel of a syringe to a first linear actuator and the piston of the syringe to a second linear actuator. The actuators are controllable to move the syringe as a unit along a path. The actuators are also controllable to move the piston relative to the barrel for drawing a grease sample into the syringe or expelling the grease sample from the syringe. The actuators move the syringe to one or more measuring positions along the path to measure one or more physical properties of the grease in the syringe.

19 Claims, 3 Drawing Sheets

GREASE MEASUREMENT DEVICE AND METHOD

RELATED APPLICATION

This application claims the benefit of and priority to U.S. patent application Ser. No. 63/142,096 filed Jan. 27, 2021 and entitled "Grease Measurement Device and Method", which priority application was co-pending on the filing date of this application and is incorporated by reference herein.

FIELD OF THE DISCLOSURE

The disclosure relates generally to a device that measures a physical property of a grease sample, and a method for obtaining the grease sample.

BACKGROUND OF THE DISCLOSURE

A lubricating grease typically behave as a non-Newtonian fluid in that the viscosity of the grease is not constant. The viscosity depends on the shear stress applied to the grease, the shear rate at which the stress is applied, and the temperature of the grease when the shear stress is applied.

A lubricating grease also do not flow like Newtonian fluids such as oil and water. Thus fluid monitoring systems such as the fluid monitoring system disclosed in Gillette II et al. Patent Application Publication 2017/010230 that rely on turbulent flow of fluid cannot be used with lubricating greases.

Instead, to acquire a sample of grease from a grease-lubricated component for measuring physical properties of the grease, the grease sample must typically be cored or separated by vacuum from the other grease in the component.

GREASE THIEF is a US registered trademark owned by the applicant for a device to acquire a grease sample for subsequent measuring of physical properties from a grease-lubricated component such as a bearing, gear, valve actuator, electric motor housing, bushing, or lubricated sliding surface, namely, a non-medical syringe.

Wurzback U.S. Pat. No. 7,984,661 "Grease sampling kit, grease sampling devices made from the kit, and related methods" is incorporated by reference as if fully set forth herein. The '661 patent discloses the syringe referred to in the immediately preceding paragraph and the method of using the syringe.

The syringe includes a tubular barrel and a piston sealing the barrel. The barrel is inserted into a reservoir or source of grease. The piston is moved away from the grease causing a grease sample to be drawn into the barrel.

It would be desirable to automate the obtaining and measuring physical properties of a grease sample from a grease-lubricated component over the life of the component.

SUMMARY OF THE DISCLOSURE

Disclosed is a method for automatically measuring a property of a grease sample obtained from a grease-lubricated component. A possible embodiment of the method includes the steps of obtaining a grease sample from a source of grease lubricating the component (the component may be a bearing, gear, valve actuator, electric motor housing, bushing, lubricated sliding, or the like), moving the grease sample along a path from the source of grease to a measuring position, measuring a physical property of the grease sample at the measuring position, and returning the grease sample back to the source of the grease.

In variant embodiments of the disclosed method, the grease sample may be positioned at more than one measuring positions along the path, a physical property of the grease sample at each measuring position.

In a further variant of the disclosed method, all or a portion of the grease sample may be collected for further analysis, archiving, or the like instead of being returned to the source of grease.

In an embodiment of the disclosed method, the inductance of the grease sample is measured. In another embodiment of the disclose method, colorimetry analysis of the grease sample may be performed. In yet another embodiment of the disclosed method, the consistency of the grease of the grease sample may be measured.

An embodiment of a device for carrying out the disclosed method includes a syringe for obtaining the grease sample, a pair of linear actuators connected to the syringe, and the measurement equipment required to make the measurement of a physical property of the sample of grease.

The measurement equipment, in an illustrative embodiment of the device, is an inductor coil defining an interior volume that can receive the syringe. The inductor coil is used to measure the inductance of the grease sample. To prevent grease from contaminating the inductor coil, the device further includes a wiper seal to remove grease from the outside of the syringe picked up while obtaining the sample of grease, The syringe includes a tubular housing or barrel having opposed first and second ends, the first end being the intake end of the barrel, a piston slideably and sealably mounted in the barrel, and a piston rod extending from the piston and out the second end of the barrel. The piston rod can be used as a handle for moving the piston towards and away the first end of the barrel.

Each linear actuator includes a shaft that translates along an axis. The shaft of one linear actuator (the barrel linear actuator) is fixedly connected to the barrel for conjoint translation of the barrel with the shaft. The shaft of the other linear actuator (the handle linear actuator) is connected to the handle for conjoint translation of the handle with the shaft.

The linear actuators can be controlled by a controller to regulate movement of the whereby both the barrel and handle translate together as a unit along a path with no relative translation of the barrel and handle with respect to one another. Alternatively, the linear actuators can be controlled whereby there is relative translation of the barrel with respect to the handle, that is, the handle can move the piston towards or away from the first end of the barrel to draw grease into the barrel or to push grease out of the barrel.

To obtain a grease sample to measure a property of the grease, the syringe is placed adjacent to a source of grease. The source of grease can be a bearing, gear, valve actuator, electric motor housing, bushing, lubricated sliding, or the like. The syringe is placed with the intake end of the syringe barrel facing the source of the grease. The intake end of the barrel is spaced about two inches away from the grease itself.

The wiper seal is similar to or can be a wiper seal used for sealing around piston rods. The wiper seal is made of an elastomeric material and has a through-hole sized slightly smaller in diameter than the barrel, and a lip surrounding the through-hole. The lip presses against the barrel and serves to wipe grease off the outside of the barrel while the barrel is disposed in the through-hole and the intake end of the syringe is moving towards the through-hole.

The syringe piston is closely adjacent to or flush with the intake end of the barrel. The syringe can be placed adjacent to or flush with the intake end of the barrel before placing the syringe adjacent to the source of grease, or can be positioned relative to the barrel after placing the syringe adjacent to the source of grease. Piston movement can be made manually before attaching the linear actuators to the handle and barrel, or can be made using the linear actuators to move the piston to the intake end of the barrel while holding the barrel stationary.

The syringe is in its standby position when placed adjacent to the source of grease with the intake end facing the source of grease and spaced from the grease, and with the piston adjacent to or flush with the first end of the barrel as described above.

With the syringe in its standby position, the inductor coil is placed relative to the syringe such that a side of the coil facing the barrel is placed flush with the second end of the barrel, the barrel aligned with the air core of the inductor coil.

The linear actuator shafts are attached to the syringe barrel and the syringe handle respectively. The linear actuator shafts have sufficient range of movement to enable moving the syringe as a unit along a path from its standby position to a grease intake position, and from the intake position to a measurement position for measuring a property of the grease sample, and from the measurement position to a grease discharge position, and then from the grease discharge position back to the standby position as described below.

To obtain a grease sample, the syringe is moved as a unit by the linear actuators from the standby position of the syringe to its intake position wherein the intake end of the barrel is immersed into the grease. The intake end of the syringe first passes through the wiper seal as the syringe moves to its intake end. The wiper seal surrounds the barrel when the syringe is in its intake position. The outer surface of the barrel is formed as a smooth, circular cylinder so that the wiper seal can closely conform to the outside of the barrel as the syringe passes through the wiper seal.

The piston rod is retracted by the handle linear actuator while the barrel remains stationary. The piston rod moves towards the second end of the barrel. The piston rod is retracted a sufficient distance based on the inside diameter of the barrel to reliably draw into the barrel a sufficient sample of grease for measuring the desired physical properties. The syringe is now in its sampling position.

After drawing a sample of grease into the syringe, the syringe is moved as a unit from its sampling position to its measurement position inside the air core of the inductor coil. The syringe fully passes through the wiper seal when moving to the measurement position, the wiper seal lip cleaning grease from the outer surface of the syringe barrel.

Referring to the inductor coil embodiment, when the syringe is in the measurement position, the syringe is located sufficiently within the measurement zone of the inductor coil. The syringe should substantially fill the air core. The diametrical clearance between the outside of the syringe and the inner turns of the inductor coil should be one-quarter inch or less to enhance the signal-to-noise ratio of the inductance measurement. The inductor coil may include a thin-walled internal plastic well or cylinder that protects the inside of the inductor coil from contamination. The syringe must clear any internal protection as well as the inductor coil itself when moving into and out of the inductor coil.

The measurement of the inductance of the inductance coil when the syringe is inside the core measures the effect of the grease sample on inductance. Current is passed through the inductor coil with the syringe in the core, and a measure of the inductance is taken.

After the inductance measurement is taken, the syringe is moved as a unit back from its measurement position to its sampling position. The piston rod is extended by the handle linear actuator while the barrel remains stationary to return the syringe to its sampling position. The piston forces all the grease out of the barrel and returned back to the source of grease.

The syringe is now in its sampling position but with the grease expelled from the barrel. The syringe is now moved as a unit from the sampling position back to its standby position to complete a measurement cycle. The wiper seal removes grease from the outside of the barrel as the syringe moves back to its standby position.

Increases in the measured inductance of the inductor coil with the syringe acting as a core may signal, for example, metallic contamination of the grease indicating bearing wear or the like.

The frequency of carrying out the disclosed method may be relatively low while the grease is new, and should increase as the grease ages or if the inductance measurements demonstrate a change in grease properties.

The device in variant embodiments may measure other physical properties of the grease sample in addition to or instead of inductance. The additional measuring positions are placed along the path defined by the linear actuators.

For example, the syringe may be positioned at a measurement position for colorimetry measurement wherein light is transmitted through the grease sample in the barrel as disclosed in U.S. Pat. No. 10,627,387 or publicly available U.S. patent application Ser. No. 15/135,116, both of which are incorporated herein by reference.

As another example, a measuring position may be coincident with another station. For example, an adjustable shutter is provided on or immediately adjacent the intake end of the barrel that defines a variable orifice. The orifice can be set at a predetermine flow area that restricts flow of grease out of the barrel. Measuring the force required for the piston to push the grease through the restricted flow orifice when discharging the grease sample at the sampling position correlates with the consistency of the grease.

In yet further embodiments of the device, a grease extraction station may be positioned along the path of movement. At the grease extraction station, the linear actuators act to have the piston push and expel grease out from the first end of the barrel. The grease from the syringe can fall onto a collecting dish or the like. The collecting dish may be positioned on a conveyor to move the grease obtained from the syringe to another location. Typically the grease is expelled at the grease extraction station after all in-barrel measurements of the grease have been conducted.

In yet further variant embodiments of the device, the apparatus may be designed to replace a used syringe with a new syringe before starting a new measurement cycle. The linear actuator Other objects and features of the disclosure will become apparent as the description proceeds, especially when taken in conjunction with the accompanying drawing sheet illustrating one or more illustrative embodiments.

DETAILED DESCRIPTION

Figure 1:
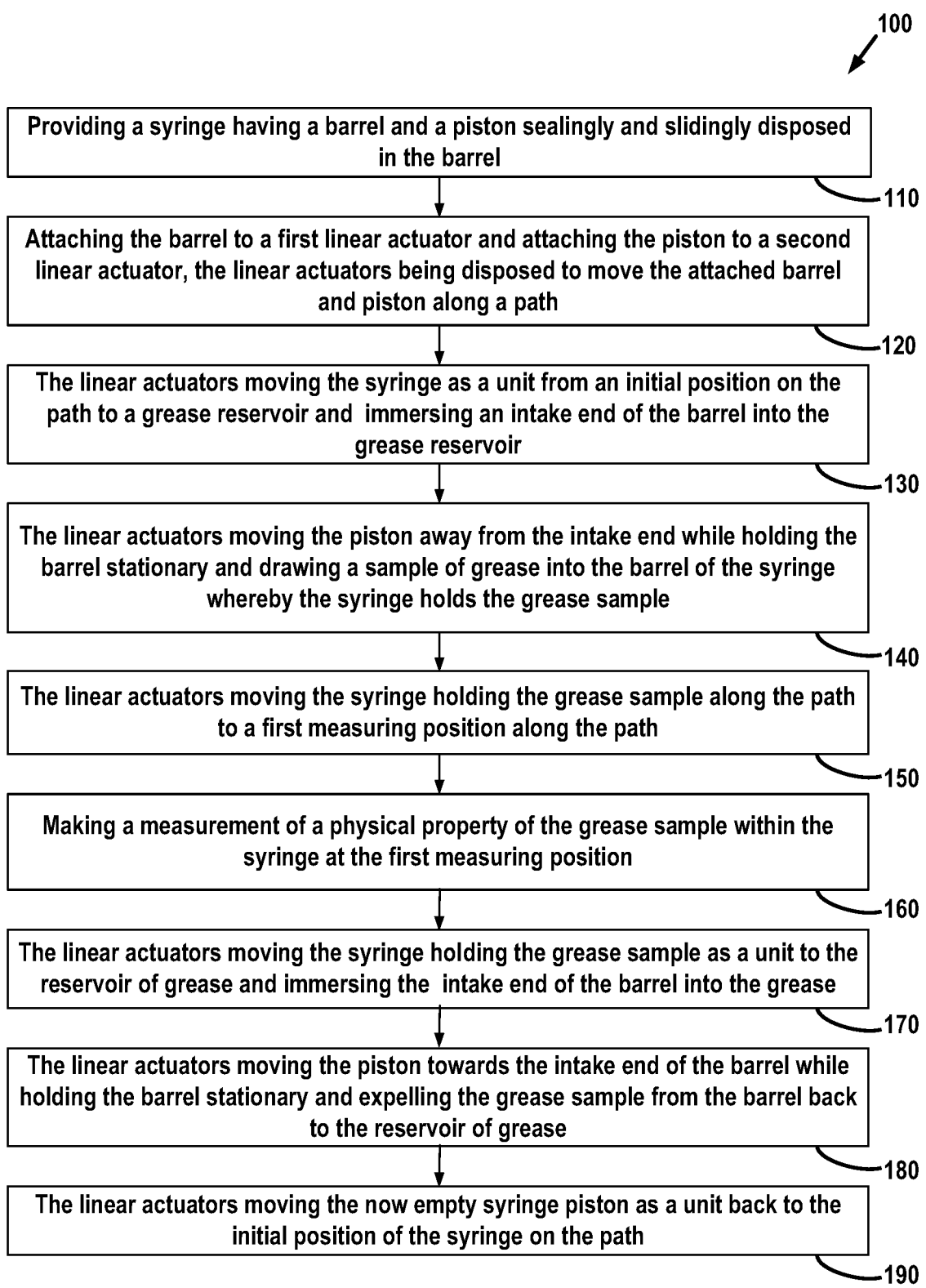
FIG. 1 illustrates the steps of an embodiment of the disclosed method for obtaining and measuring at least one physical property of a grease sample in accordance with this disclosure.

FIG. 1 illustrates the steps of a method 110 for obtaining and measuring at least one physical property of a sample of grease obtained from a reservoir of grease such as the grease contained in a grease-lubricated component.

The method includes the steps of:

Step 110: Providing a syringe having a barrel and a piston sealingly and slidingly disposed in the barrel;

Step 120: Attaching the barrel to a first linear actuator and attaching the piston to a second linear actuator, the linear actuators being disposed to move the attached barrel and piston along a path;

Step 130: The linear actuators moving the syringe as a unit from an initial position on the path to a grease reservoir and immersing an intake end of the barrel into the grease reservoir;

Step 140: The linear actuators moving the piston away from the intake end while holding the barrel stationary and drawing a sample of grease into the barrel of the syringe whereby the syringe holds the grease sample;

Step 150: The linear actuators moving the syringe holding the grease sample along the path to a first measuring position along the path;

Step 160: Making a measurement of a physical property of the grease sample within the syringe at the first measuring position;

Step 170: The linear actuators moving the syringe holding the grease sample as a unit to the reservoir of grease and immersing the intake end of the barrel into the grease;

Step 180: The linear actuators moving the piston towards the intake end of the barrel while holding the barrel stationary and expelling the grease sample from the barrel back to the reservoir of grease; and Step 190: The linear actuators moving the now empty syringe piston as a unit back to the initial position of the syringe on the path.

The method can be modified as previously described above. For non-limiting examples, the grease sample can be partially or entirely expelled from the syringe into a container instead of being entirely returned to the grease reservoir. Additional measuring positions can be provided along the actuator path.

Figure 2:
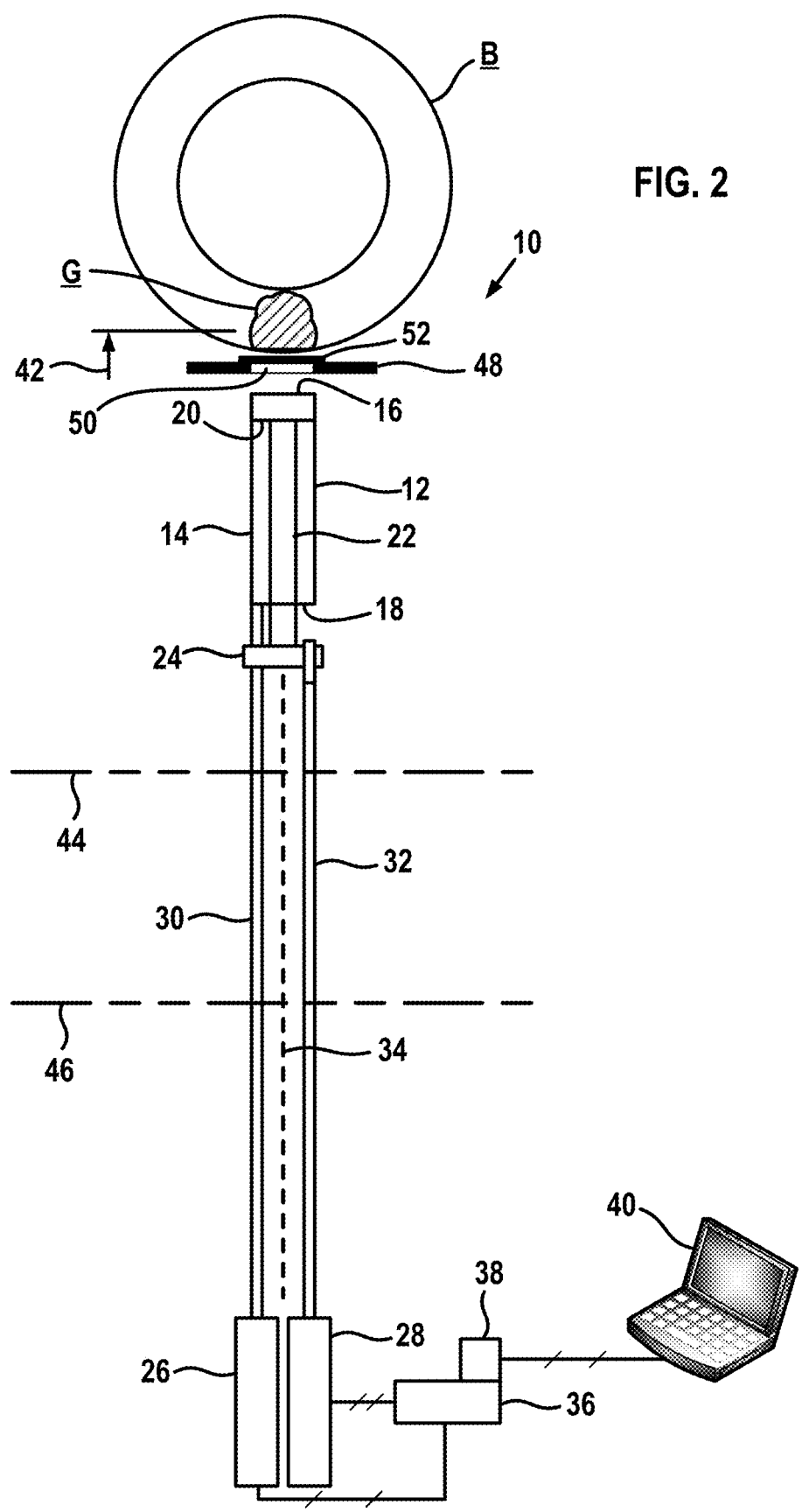
FIG. 2 illustrates a device for obtaining and measuring at least one physical property of a grease sample in accordance with this disclosure.

FIG. 2 illustrates a device 10 that automates the method for obtaining and measuring at least one physical property of a sample of grease obtained from a grease-lubricated component. The device 10 is shown used to obtain a grease sample from a bearing B lubricated by a reservoir of grease G. The bearing has a port (not shown) that provides access to the grease G for retrieving the grease sample.

The device 10 includes a syringe 12 having a circularly cylindrical barrel 14 extending axially from a first open end 16 to an opposite end 18. A piston 20 is sealingly disposed inside the barrel 14. A piston rod 22 extends from the piston 20. The piston rod extends out the barrel end 18 to a handle 24 formed on the free end of the piston rod and disposed outside of the barrel.

The device 10 further includes a first electrical linear actuator 26 and a second electrical linear actuator 28. The first actuator has a movable shaft 30 fixedly attached to the barrel 14. The second actuator has a movable shaft 32 fixedly attached to the handle 14. The connections between the shafts and the syringe 12 may be via threaded connections, press fits, interference fits, keyed connections, adhesives, and the like.

The first actuator will be referred to as the barrel actuator 26 and the second actuator will be referred to as the handle actuator 28 herein. The two actuator shafts extend parallel with one another along a linear path 34 that is co-axial with the center of the barrel 14.

The barrel actuator 26 and the handle actuator 28 are both connected to a controller 36 that controls axial movement of both actuator shafts. A controllable linear actuator has sensor (s) that provide a signal indicating the distance the shaft is extended and the speed the shaft is traveling. Control of the linear actuator requires wiring the linear actuator to a controller that can communicate with the linear actuator through a control interface or process control bus, depending on the manufacturer and type of linear actuator being used. The controller 36 is designed to communicate with and control both the linear actuators 26, 28 as is known in the linear actuator art.

The controller 36 also communicates externally via an I/O port or process control bus 38 connected to a user operated computer or microprocessor 40 for programming of the actuators and to otherwise enable a user to control operation of the actuators in moving and stopping the syringe 12 along the path 34 as will be described in further detail below.

The controller 36 is programmed to move the syringe 12 as a unit (no relative motion between the barrel 14 and the piston 20) along the path 34 between the barrel and handle actuators 26, 28 and a terminal path end 42. In the illustrated embodiment the controller is programmed to stop the syringe 12 at two measuring positions 44, 46 along the path 34.

The measuring positions are where measurements of physical properties of a grease sample held in the syringe 12 takes place. When the measurement at the first position 44 is complete, the user can command the controller to move the syringe from the first measuring position to the second measuring position or taking the second measurement.

The controller 36 is also programmed to maintain the barrel 14 stationary along the path 34 while moving the piston 20 away from or towards the first barrel end 18 to draw grease into the barrel or to expel grease out of the barrel.

FIG. 2 illustrates the syringe 12 in its standby position along the path 34 prior to starting a cycle obtaining a grease sample from the grease reservoir G, making measurements at the measuring positions 44, 46, emptying the syringe of the grease sample, and returning the syringe to the standby position. The syringe is empty and the piston 20 is substantially flush with the first barrel end 18.

To obtain a grease sample, the syringe is moved as a unit by the linear actuators from the standby position of the syringe to its intake position wherein the open barrel end 18 is located at the path terminal end 42. The barrel end 18 is immersed in the grease reservoir G.

The piston 20 is retracted by the piston actuator 28 while the barre actuator 26 holds the barrel stationary. The piston moves towards the second barrel end 18. The piston is retracted a sufficient distance based on the inside diameter of the barrel to reliably draw into the barrel a sufficient sample of grease for measurements. The syringe is now in its sampling position after having loaded a grease sample and will now be moved as a unit to the first measuring position 44.

Because the syringe has been immersed in grease, the outer surface of the barrel 14 will be coated with grease. The illustrated device 10 includes a wiper seal 48 on the path 42 between the standby position of the syringe and the bearing B. The wiper seal includes a circular through-hole 50 that is stretched by the syringe passing through the hole, and a lip 52 surrounding the through-hole. The lip presses against the barrel and serves to wipe grease off the outside of the barrel as the syringe moves to the first measuring position. An example of a piston wiper seal that can be adapted for use with the device 10 is disclosed in Castleman et al. U.S. Pat. No. 8,387,990 "Seal Assembly" which is incorporated by reference herein.

A property measurement of the grease sample is made at the first measuring position 44, and the user next commands the controller 36 to move the syringe as a unit to the second measurement station 46.

After a property measurement of the grease sample is made at the second position 44, the user next commands the controller 36 to move the syringe 12 as a unit back to the path terminal end 42 and expel the grease from the syringe. The piston actuator 28 moves the piston 20 back to the first barrel end 16 to expel the grease back into the reservoir while the barrel actuator 26 holds the barrel stationary.

After the grease has been expelled, the syringe 12 is moved back to its standby position as shown in FIG. 1 to complete the cycle. The syringe 12 again passes through the wiper 48 to remove grease from the outside of the barrel 14.

Figure 3:
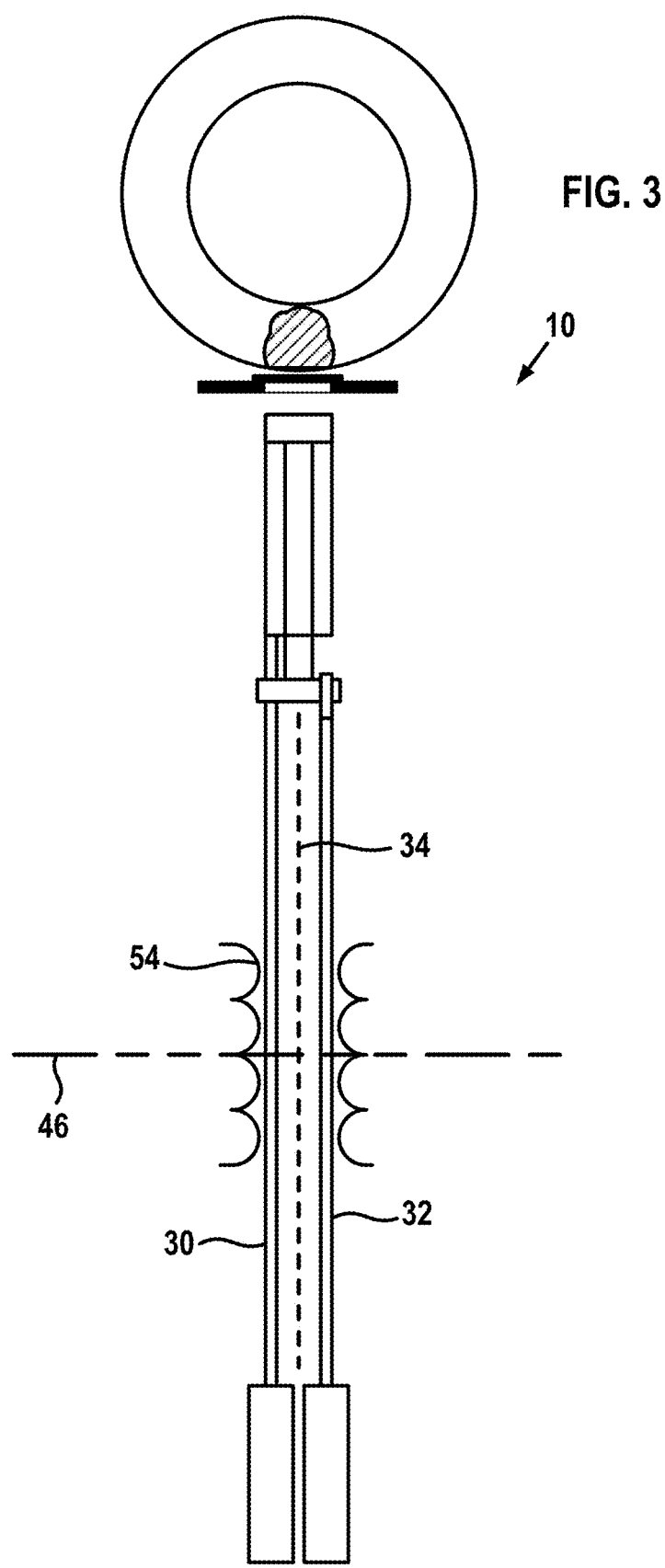
FIG. 3 illustrates the device shown in FIG. 2 having an inductor coil located at a measuring position.

FIG. 3 is a simplified drawing of the device 10 wherein the device 10 includes an inductor coil 54 located at second measuring position 48 on the actuator path 34. The inductor coil has an air core and includes a number of turns of conductor wire wound around the air core. The actuator shafts 30, 32 pass through the air core. The inductor coil is positioned to closely receive the syringe barrel 14h when the syringe is at the second measuring position.

Figure 4:
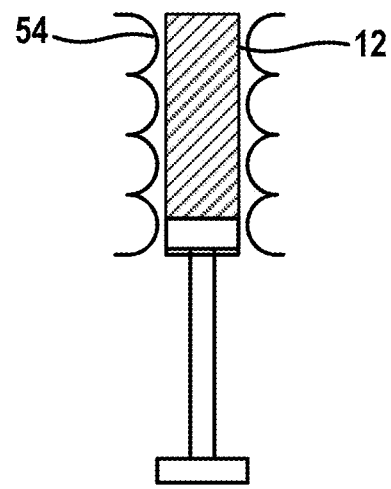
FIG. 4 is an enlarged view of the device shown in FIG. 3 illustrating aa syringe holding a grease sample disposed in the core of the inductor coil.

FIG. 4 illustrates the syringe 12 filled with the grease sample being closely received in the inductor coil 54. The measurement of the inductance of the inductance coil when the syringe is inside the core measures the effect of the grease sample on inductance and for evaluation purposes when comparing multiple measurements taken over time can be considered the inductance of the grease sample.

Embodiments of the device 10 may include other types of measuring equipment located at measuring positions along the actuator path as previously described above.

Yet other embodiments of the device 10 the controller 36 may issue a signal to the computer 40 that the syringe 12 has reached a measuring position in order for the computer to initiate the measurement process on the grease sample at the measurement station, thereby totally automating a measurement cycle. The controller 36 may also be interconnected itself with the measurement equipment to initiate the measurement process on its own.

The controller 36 in other embodiments of the device 10 is programmed to initiate a measurement on a predetermined schedule, the frequency which may change over time or based on the results of the measurements. The measurements can be useful as input data to a diagnostic module or an artificial intelligence module to evaluate the condition of the bearing B and its expected lifetime, the condition of the grease in the reservoir G and its expected lifetime, and the like.

While this disclosure includes one or more illustrative embodiments described in detail, it is understood that the one or more embodiments are each capable of modification and that the scope of this disclosure is not limited to the precise details set forth herein but include such modifications that would be obvious to a person of ordinary skill in the relevant art including (but not limited to) changes in material selection, size, operating ranges, environment of use, and the like.

What is claimed is:

1. A method for obtaining and measuring at least one physical property of a sample of grease obtained from a reservoir of grease, the method comprising the steps of:
   (a) providing a syringe having a barrel and a piston sealingly and slidingly disposed in the barrel;
   (b) attaching the barrel to a first linear actuator and attaching the piston to a second linear actuator, the linear actuators being disposed to move the attached barrel and piston along a path;
   (c) the linear actuators moving the syringe as a unit from an initial position on the path to a grease reservoir and immersing an intake end of the barrel into the grease reservoir;
   (d) the linear actuators moving the piston away from the intake end of the barrel while holding the barrel stationary and drawing a sample of grease into the barrel of the syringe whereby the syringe holds the grease sample;
   (e) the linear actuators moving the syringe holding the grease sample along the path to a first measuring position along the path;
   (f) performing a measurement of a physical property of the grease sample within the syringe at the first measuring position;
   (g) the linear actuators moving the piston towards the intake end of the barrel while holding the barrel stationary and expelling the grease sample from the barrel and emptying the syringe of grease; and
   (h) the linear actuators moving the now empty syringe piston as a unit back to the initial position of the syringe on the path.

2. The method of claim 1 wherein after step (f) and prior to step (g), the method comprises the step of:
   (i) the linear actuators moving the syringe holding the grease sample as a unit to the grease reservoir and immersing the intake end of the barrel into the grease reservoir.

3. The method of claim 1 wherein the grease reservoir contains grease lubricating a grease-lubricated component.

4. The method of claim 1 wherein the grease-lubricated component is a bearing.

5. The method of claim 1 wherein step (g) comprises the step of:
   (i) ejecting some or all of the grease sample from the syringe; and
   (j) collecting the ejected grease and not returning the collected grease to the grease reservoir.

6. The method of claim 5 wherein step (i) comprises ejecting some but not all of the grease sample from the syringe whereby the syringe holds a remaining amount of the grease sample after performing step (i), and the method further comprises the steps of:
   (k) the linear actuators moving the syringe holding the remaining amount of the grease sample as a unit to the grease reservoir and immersing the intake end of the barrel into the grease reservoir; and (l) the linear actuators acting to eject the remaining amount of the grease sample from the syringe and into the grease reservoir.

7. The method of claim 1 wherein step (e) comprises the step of:
  (i) the linear actuators moving the syringe into an air core of an inductor coil.

8. The method of claim 7 wherein step (f) comprises the step of:
  (j) measuring the inductance of the inductor core with the syringe in the core of the inductor coil.

9. The method of claim 1 wherein step (f) comprises transmitting light through the grease sample held in the syringe and performing colorimetry analysis using the transmitted light.

10. The method of claim 1 wherein step (g) comprises the step of measuring the force applied to the piston to move the piston while the piston is expelling grease from the syringe.

11. A device for obtaining and measuring at least one physical property of a sample of grease obtained from a reservoir of grease, the device comprising:
  a syringe, a first linear actuator and a second linear actuator, and a controller connected to the first and second linear actuators and capable of communicating with and controlling the linear actuators;
  the syringe comprising a barrel, a piston sealingly and slidingly disposed in the barrel, the barrel extending axially from an open first end to an opposite second end, the piston movable between an extended position substantially flush with the first end of the barrel and a retracted position spaced from the extended position towards the second end of the barrel, the piston rod extending from the piston and out the second end of the barrel when the piston is in either the extended or retracted position;
  each linear actuator comprising a shaft drivable by the linear actuator for axial movement of the shaft;
  the shaft of the first linear actuator being connected to the barrel of the syringe for conjoint axial movement of the shaft and barrel;
  the shaft of the second linear actuator being connected to the piston of the syringe for conjoint axial movement of the shaft and piston;
  the linear actuators being controllable to move the syringe as a unit without relative displacement of the barrel and piston with respect to one another along a path; and
  linear actuators being controllable to move the piston along the path while holding the barrel stationary on the path;
  wherein the linear actuators are controllable to move the syringe as a unit from a standby position along the path to a second position along the path spaced from the standby position and hold the barrel stationary at the second position; and
  wherein the linear actuators are controllable to move the syringe as a unit from the second position along the path to one or more measuring positions along the path, the device capable of measuring a property of a grease sample held in the syringe when the syringe is disposed at one of the one or more measuring positions.

12. The device of claim 11 wherein the first end of the barrel faces away from the actuators.

13. The device of claim 11 wherein the device comprises an inductor coil having an air core, the inductor coil being disposed at one of the one or more measuring positions, the barrel of the syringe being received in the air core when the syringe is disposed at the inductor coil measuring station.

14. The device of claim 13 wherein the shafts of the linear actuators are extendable through the air core of the inductor coil.

15. The device of claim 11 wherein the linear actuators are controllable to retract the piston away from the first end of the barrel when the syringe is in the second position.

16. The device of claim 15 wherein the first end of the barrel is immersed in a grease reservoir when the syringe is disposed in the second position.

17. The device of claim 15 wherein the linear actuators are controllable to extend the piston towards the first end of the barrel when the syringe is in the second position.

18. The device of claim 11 wherein the linear actuators are controllable to hold the syringe at a standby position along the path disposed between the one or more measuring positions and the second position.

19. The device of claim 11 wherein the second actuator is attached to the piston rod for connection to the piston.

* * * * *